United States Patent
Cullen et al.

(10) Patent No.: US 7,330,763 B1
(45) Date of Patent: Feb. 12, 2008

(54) METHOD FOR SECURING THE OPERATING SYSTEM IN A HANDHELD MEDICAL DEVICE AND APPARATUS

(75) Inventors: Patrick M. Cullen, Dallas, TX (US); Yan Wei Shi, Plano, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 653 days.

(21) Appl. No.: 10/426,569

(22) Filed: Apr. 30, 2003

(51) Int. Cl.
*A61N 1/00* (2006.01)

(52) U.S. Cl. ...................................................... 607/59

(58) Field of Classification Search ............ 607/30–32, 607/60, 59
See application file for complete search history.

(56) References Cited

U.S. PATENT DOCUMENTS 5,938,690 A    8/1999   Law et al.
6,381,496 B1 *  4/2002   Meadows et al. ............. 607/59
6,893,395 B1 *  5/2005   Kraus et al. ................. 600/300
2002/0049480 A1 *  4/2002   Lebel et al. .................. 607/60
2002/0123673 A1 *  9/2002   Webb et al. ................ 600/300
2003/0144711 A1 *  7/2003   Pless et al. ................... 607/60
2006/0112427 A1 *  5/2006   Shahbazi ..................... 726/16

* cited by examiner

*Primary Examiner*—Scott M. Getzow
(74) *Attorney, Agent, or Firm*—Christopher S. L. Crawford; Peter Lando; Melissa Acosta (57) ABSTRACT

A method includes disabling a synchronization mechanism of a handheld device and disabling one or more hardware buttons on the handheld device. The method also includes removing user access to one or more settings on the handheld device. In addition, the method includes removing one or more system functions on the handheld device.

7 Claims, 4 Drawing Sheets

METHOD FOR SECURING THE OPERATING SYSTEM IN A HANDHELD MEDICAL DEVICE AND APPARATUS

TECHNICAL FIELD

This disclosure is generally directed to handheld computer systems and more specifically to a method for securing the operating system in a handheld medical device and apparatus.

BACKGROUND

Small computing devices, commonly referred to as "handheld devices" or portable computing devices, have become more common as the processing power of the devices has increased (referred to as a "handheld device"). Such devices are increasingly being used in the medical field. For example, a handheld medical device could be given to a patient in a hospital, and the patient may use the device to record when the patient experiences pain or to control the dispensing of pain medication. A typical handheld device generally functions using an operating system that supports various functions and includes functionality allowing a user to load additional programs (or modify existing programs) into the devices. One problem with conventional handheld devices is that the execution of one program may cause interference with, or affect, the execution of another program on the device. Moreover, with the capability of downloading or modifying programs, a user or other unauthorized person may be able to load new programs, modify existing programs, or interfere with the operation of the handheld device, either intentionally or inadvertently, thus interfering with the operation of the handheld device. Such interference may be inconvenient during normal use but may cause serious problems when the device is used in a medical environment.

SUMMARY

This disclosure provides a method for securing the operating system in a handheld medical device and apparatus.

In one embodiment, a method includes disabling a synchronization mechanism of a handheld device and disabling one or more hardware buttons on the handheld device. The method also includes removing user access to one or more settings on the handheld device. In addition, the method includes removing one or more system functions on the handheld device.

In another embodiment, an apparatus includes a memory operable to store a medical program. The apparatus also includes a processor operable to execute the medical program and an operating system. The operating system is secured so as to limit interference with the execution of the medical program.

One or more technical features may be present according to various embodiments of this disclosure. Particular embodiments of this disclosure may exhibit none, some, or all of the following features depending on the implementation. For example, in one embodiment, a method for securing the operating system in a handheld medical device is provided. In particular, one or more medical programs are loaded into the device, and various features of the device that may interfere with the medical programs are disabled. This may help to reduce or eliminate the likelihood that some feature of the handheld device will interfere with the operation of the medical programs. This may also help to reduce or eliminate the ability for someone to maliciously tamper with the handheld device.

Moreover, conventional handheld devices are typically reset when power is lost. This typically restores the factory default settings of the conventional handheld devices. To help prevent the medical handheld device from being reset due to a power loss, a procedure to disable the various features of the device may be stored in non-volatile memory. The procedure may then be automatically executed when power is restored to the handheld device. In this way, the handheld device may be properly configured even after a power loss.

This has outlined rather broadly several features of this disclosure so that those skilled in the art may better understand the DETAILED DESCRIPTION that follows. Additional features may be described later in this document. Those skilled in the art should appreciate that they may readily use the concepts and the specific embodiments disclosed as a basis for modifying or designing other structures or methods for carrying out the same purposes of this disclosure. Those skilled in the art should also realize that such equivalent constructions do not depart from the spirit and scope of the invention in its broadest form.

BRIEF DESCRIPTION OF THE DRAWINGS

For a more complete understanding of this disclosure and its features, reference is now made to the following description taken in conjunction with the accompanying drawings, in which.

DETAILED DESCRIPTION

Figure 1:
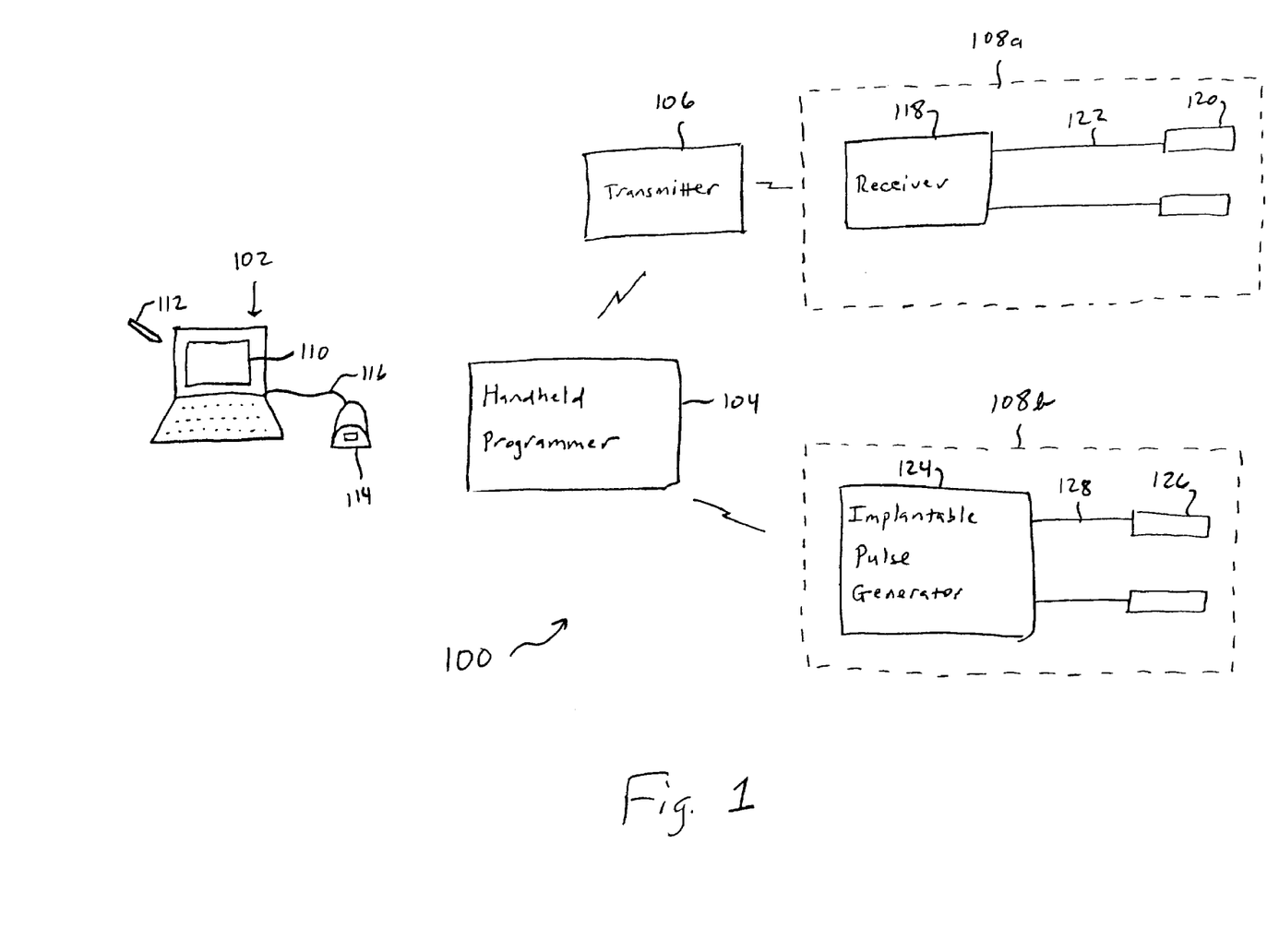
FIG. 1 illustrates an example medical system according to one embodiment of this disclosure.

FIG. 1 illustrates an example medical system 100 according to one embodiment of this disclosure. In the illustrated example, the system 100 includes a base computer 102, a handheld programmer 104, a transmitter 106, and one or more types of implanted components 108a and 108b. Other embodiments of the medical system 100 may be used without departing from the scope of this disclosure.

The base computer 102 stores and executes one or more programs used in a medical environment. For example, the base computer 102 could execute an application to collect information from a patient, such as symptoms of the patient or insurance information. In one embodiment, a user inputs information into the base computer 102 by touching the screen 110 of the computer 102 with a stylus 112 or by using another input device (such as a keyboard, mouse, infrared, RF, data communications, and the like, or any other means capable of user input). In the illustrated example, the base computer 102 represents a laptop computer operating using an operating system, and in one embodiment, the operating system may be a Windows-based operating system. Any other computing device (such as a desktop computer) may be used as a base computer 102 in the medical system 100.

The handheld programmer 104 communicates (via wire or wireless) with the base computer 102, the transmitter 106, and the implanted component 108b. The handheld programmer 104 may be any computing device and, in the example embodiment, is a handheld device. In one embodiment, the handheld programmer 104 may be of the type known as personal digital assistant (PDA), and may be the same or similar to PDAs sold by such manufacturers as Palm, Dell, Compaq, HP, IBM, etc. However, the handheld programmer 104 is not limited to a PDA, and any computing device having the desired capabilities may be used.

The handheld programmer 104 generally includes an operating system and one or more loaded programs. In an example embodiment, one of the loaded programs is a medical program. A medical program may be any type of program (that includes instructions) related to the medical field or functioning for any medical purposes, including pain management. The medical program, when executed or in operation within the handheld programmer 104, operates to directly or indirectly control the operation of the transmitter 106 and the implanted components 108a and 108b. The handheld programmer 104 communicates directly with the implanted component 108b or indirectly with the implanted component 108a through the transmitter 106. In a particular embodiment, and as will be appreciated, some or all of the functions performed by the base computer 102 may be implemented in the handheld programmer 104.

The handheld programmer 104 is illustrated as communicating with the transmitter 106 or implanted components 108a, 108b. The handheld programmer 104 communicates with the transmitter 106 or implanted components 108a, 108b using any suitable mechanism or method, such as wireline or wireless. One example embodiment of a handheld programmer 104 is shown in FIGS. 2A through 2D, which are described below.

In the illustrated embodiment in FIG. 1, a docking cradle 114 facilitates communication between the base computer 102 and the handheld programmer 104. In a particular embodiment, the base computer 102 and the docking cradle 114 are coupled by a universal serial bus (USB) cable 116. In general terms, data is transferred between the base computer 102 and the handheld programmer 104 when a user places the handheld programmer 104 in the docking cradle 114. This illustrates one example mechanism for facilitating communication between the base computer 102 and the handheld programmer 104. Other mechanisms, such as a serial cable, infrared link, radio frequency link, or ultrasonic sound link, could be used.

The transmitter 106 communicates information to the implanted component 108a. For example, the transmitter 106 could communicate information providing data or a program instructing operation or functionality of the implanted component 108a. The transmitter 106 may be any device capable of communicating with the implanted component 108a, and may be any suitable transmitter, such as a radio frequency transmitter.

The implanted components 108a, 108b are representative of components implanted into a body or patient. In this example embodiment, the implanted components 108a, 108b are utilized to perform stimulation, such as spinal cord stimulation or stimulation of other tissue or areas of the body. Such stimulation involves delivering electrical pulses to various portions of the body. More specifically, spinal cord stimulation applies electrical pulses to spinal cord areas. Such stimulation or treatment is also referred to as "neuromodulation." Overall control of the stimulation is generally performed by the handheld programmer 104. Thus, the handheld programmer 104 is a controller that functions to directly or indirectly control the stimulation through control of the transmitter 108, the implanted components 108a, or the implanted components 108b.

Different types of medical components could be used to deliver the electrical pulses. As shown in FIG. 1, the implanted component 108a includes a receiver 118 and one or more electrodes 120 coupled to the receiver 118 by one or more leads 122 (e.g. percutaneous, lamitrode, etc.). Typical operation of the implanted component 108a is controlled by one or more of the transmitter 106 and the handheld programmer 104. In the example embodiment, the handheld programmer transmits signals (e.g., data, software program, etc.) to the transmitter 106. In turn, the transmitter 106 transmits control signals to the receiver 118, which produces electrical pulses on the leads 122 in response to the received signals. As will be appreciated, the information received by the receiver 118 may include simple control signals or more complex information (such as a program). In this way, the transmitter 106 (and/or handheld programmer 104) controls the electrical pulses generated and supplied to the electrodes 120. The receiver 118 may be any device capable of communicating with transmitter 106 and generating electrical pulses, such as a radio frequency receiver. An example transmitter 106 and receiver 118 may be those manufactured by Advanced Neuromodulation Systems, Inc., such as the Renew® System, part numbers 3408, 3416, 3508, and 3516.

The electrodes 120 and the leads 122 are generally made of any suitable structure for facilitating the transmission and application of electrical pulses to areas of a body. Example electrodes and leads may be those manufactured by Advanced Neuromodulation Systems, Inc. and/or MicroNet Medical, Inc.

The implanted component 108b includes an implantable pulse generator 124, one or more electrodes 126, and one or more leads 128. The electrodes 126 and the leads 128 may be the same as or similar to the electrodes 120 and the leads 122, respectively, described above. The implantable pulse generator 124 receives signals (e.g., data, software program, etc.) from the handheld programmer 104 and generates electrical pulses on the leads 128 in response to the signals. The implantable pulse generator 124 may be any device capable of communicating with transmitter 106 and generating electrical pulses, such as a radio frequency receiver and pulse generator. An example implantable pulse generator 124 may be one manufactured by Advanced Neuromodulation Systems, Inc., such as the Genesis® System, part numbers 3604, 3608, 3609, and 3644.

While FIG. 1 illustrates two electrodes 120, 126 and two leads 122, 128 in each of the implanted components 108, any suitable number of electrodes 120, 126 and leads 122, 128 may be used. Further, any number of electrodes 120, 126 may be coupled to each lead 122, 128.

In an example embodiment, a user utilizes the base computer 102 and/or the handheld programmer 104 to collect information about a patient or body. For example, the base computer 102 could provide a list of current patients to the user, and the user could select a particular patient. After that, various procedures could be executed. For example, the base computer 102 may allow the user to execute pre-operative procedures, intra-operative procedures, and post-operative procedures. The pre-operative procedures could be used to evaluate a patient's physical and mental condition, select a particular neuromodulation system to be implanted in a patient, and determine locations for electrode placement. The intra-operative procedures could be used during the implantation and positioning of the electrodes 120, 126 and other implanted components 108 in a patient. The post-operative procedures could be used to help optimize the operational settings of the implanted components 108a and 108b (including transmitter 106).

As particular examples, the pre-operative procedures could include creating a pain map, which allows a patient or other user to identify the location and severity of pain experienced by the patient. The pre-operative procedures could also include creating dermatome and segmented dermatome charts, which identify the relationship between the reported areas of pain and the dermatomes of the human body. The pre-operative procedures could further associate the patient's pain information with affected nerve or nerve roots, which join the patient's spinal cord at particular locations. This information may be used by a physician to identify locations in which the electrodes 120, 126 may be positioned. Beyond that, the pre-operative procedures can collect information identifying the components 108 to be implanted in the patient or recommend the components 108 to be implanted. In addition, the pre-operative procedures may also include the collection and storage of other information about the patient, such as medical histories, insurance information, and physical characteristics of the patient's body.

The intra-operative procedures may include procedures to verify the placement of the electrodes 120, 126 in the patient and the effectiveness of the electrodes 120, 126. The intra-operative procedures may also allow various tests to be performed, such as manual stimulation tests, manual symmetry tests, and auto symmetry tests. A manual stimulation test allows a user to administer stimulation of the patient's spinal cord or other area. For example, the user may identify the electrodes 120, 126 to be stimulated and the frequency, pulse width, phase, and amplitude of electrical pulses delivered to the electrodes 120, 126. A manual symmetry test is used to verify electrode symmetry and assess the region of influence of the applied stimulation for each tested stimulation. For example, this may allow a physician to monitor, control, and optimize the applied electrical pulse's symmetry and region of influence. The auto symmetry test allows assessment of the symmetry and region of stimulation influence for the electrodes. The auto symmetry test may also help the physician assess the placement of the electrodes 120, 126. Results of the various tests could then be presented to the user.

The post-operative procedures may include the manual stimulation test described above. The post-operative procedures may also include a manual sequence test allowing the user to specify a new stimulation setting and how the electrical stimulation affects the patient. The post-operative procedures may further include a sequential recruitment test. This allows a single combination of parameters or a programmed sequence of combinations to be tested. Beyond that, the post-operative procedures may include a program sequence test, which allows the programming of a sequence or series of stimulation settings. The base computer 102 or handheld programmer 104 may then guide the patient through an assessment procedure, in which the patient enters data about the patient's perceptions during the assessment. In addition, the post-operative procedures could include an automatic sequence test, which involves a systematic, iterative routine used to determine and optimize the patient's stimulation settings.

In one aspect of operation, the handheld programmer 104 represents a computing device, such as a personal digital assistant or pocket personal computer. The handheld programmer 104 may operate using an operating system, such as Microsoft Windows CE. The handheld programmer 104 includes one or more medical programs for controlling the operation of the implanted components 108. The operating system in the handheld programmer 104 supports various functions and hardware that may interfere with the operation of the medical programs. Also, a user or other person might be able to load additional applications or data into the handheld programmer 104, or modify existing programs either intentionally or inadvertently, that may result in interference with the medical program (and operation thereof).

To reduce or eliminate this interference, the handheld programmer 104 may be configured to lock down the operating system. Locking down the operating system operably disables various features of the handheld programmer 104 that might interfere, or allow interference, with the medical programs. Locking down may also reduce or eliminate the ability to load additional applications onto the handheld programmer 104, or modify, change, or alter the functions and programs of the programmer 104. In this way, the medical programs, and hence functioning of the components 108, will be unalterable (or unalterable except by authorized persons). This may also help to reduce or eliminate the ability for someone to maliciously tamper or inadvertently modify or interfere with, the medical programs on the handheld programmer 104 and functioning of components 108.

In addition, a mechanism or method for storing the locking down mechanism or method in a non-volatile memory in the handheld programmer 104 is provided. With this feature, the handheld programmer 104 is configured to automatically execute the locking down mechanism or procedure when power is lost and then restored to the handheld programmer 104. This allows the handheld programmer 104 to be configured and operable with the lock down feature even after the handheld programmer 104 is reset due to a power loss, thus not requiring a reboot or reprogramming of the programmer 104.

Although FIG. 1 illustrates one example of a medical system 100, various changes may be made to FIG. 1. As will be appreciated, while FIG. 1 illustrates two separate types of implanted components 108a and 108b, only one of the implanted components 108 may be used in a body (though more than one could be used, if desired). Also, though the base computer 102 is illustrated as a laptop computer, any suitable type of computing device may be used.

FIGS. 2A through 2D illustrate an example medical device 200 according to one embodiment of this disclosure. The medical device 200 may, for example, be the programmer 104 of FIG. 1. Other computing devices could be used in the medical system 100 without departing from the scope of this disclosure. The medical device 200 may also be referred within the disclosure as a computing device, handheld device, or handheld medical device.

Figure 2A:
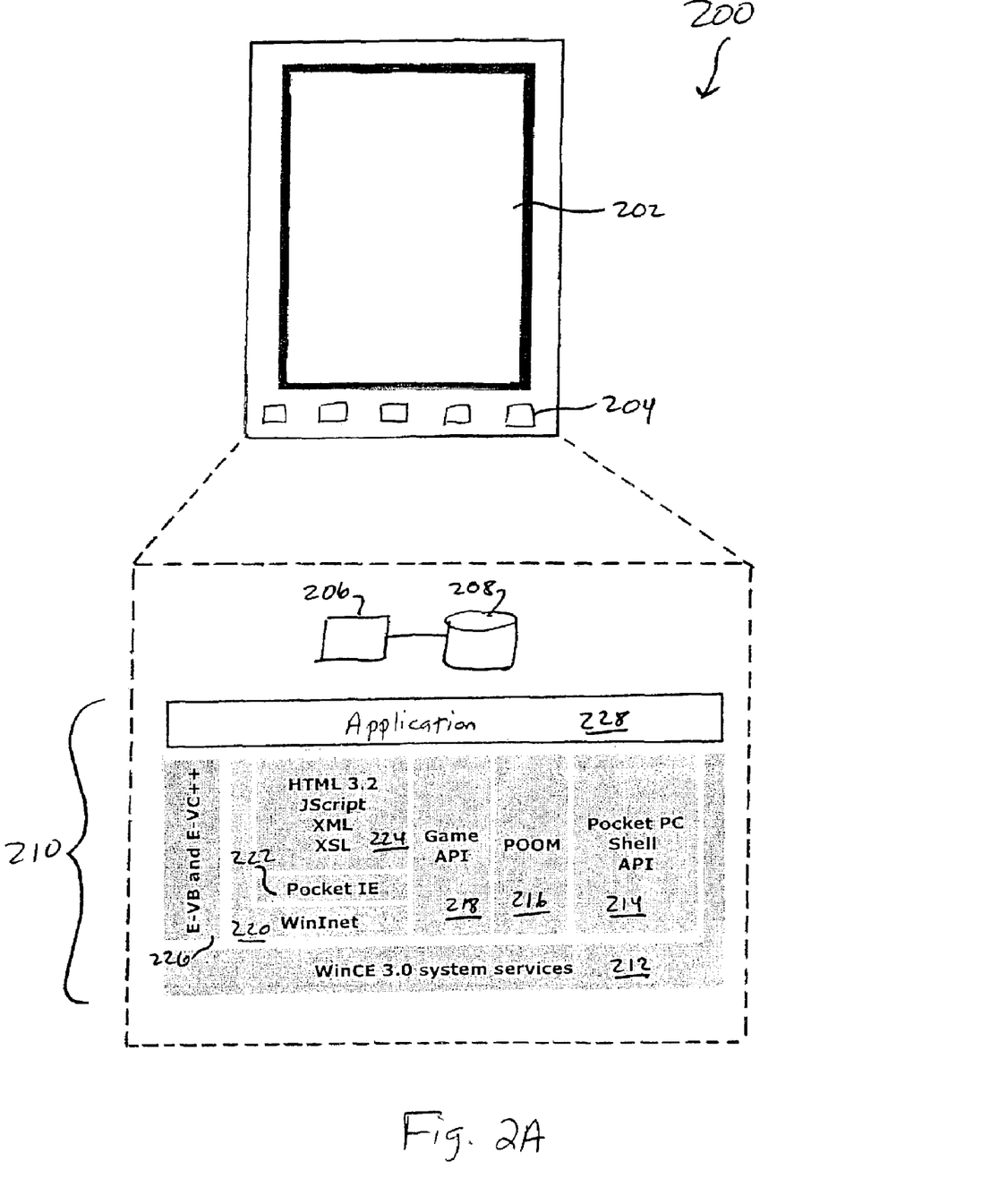
FIGS. 2A through 2D illustrate an example handheld medical device according to one embodiment of this disclosure.

With reference to FIG. 2A, the medical device 200 is shown as a personal digital assistant (PDA). As will be appreciated, the medical device 200 may include any type of computing device. In this example, the medical device 200 includes a display screen 202 and multiple buttons 204. The display screen 202 is capable of displaying information to a user. In one embodiment, the display screen 202 may present a graphical user interface to the user, such as the Windows CE graphical user interface. The buttons 204 allow the user to invoke various functions in the medical device 200. For example, one button 204 may be a power button. Other buttons 204 could invoke execution of calendar, mail, task, contact, and record functions.

The items shown in the dashed lines of FIG. 2A represent various functional components in the medical device 200.

This functional division is for illustration only. Other functional divisions could be used in the medical device 200.

In the illustrated example, the medical device 200 includes at least one processor 206 and a memory 208. The processor 206 executes applications to provide various functions to a user. The memory 208 stores instructions executed by the processor 206 and data. It will be understood that the memory 208 includes non-volatile memory and volatile memory, and any other types of memory, as desired.

The medical device 200 includes an operating system (not shown specifically). The basic operation and functionality of operating systems are well-known to those in the art. In one embodiment, the operating system may be any operating system. In a particular embodiment, the operating system is a Windows-based operating system, such as Windows CE or Windows Pocket PC.

The medical device 200 also includes an application stack 210. The components in the application stack 210 support various functions performed by the medical device 200. For example, system services 212 support various system functions in the medical device 200. More particularly, the system services 212 may implement the contacts, telephony, and graphics functions used by the medical device 200. A pocket PC shell application programming interface (API) 214 provides an interface so that various system services 212 can be invoked. For example, the pocket PC shell API 214 allows users to create desktop shortcuts, add icons to a task bar, and add items to a "recent documents" list in a Start menu.

A Pocket Outlook Object Model (POOM) 216 allows a user to manipulate contact, calendar, and task data using inbox electronic messaging software. A game API 218 supports the execution of games on the medical device 200. For example, the game API 218 may support direct access to a display memory in the medical device 200 and to the hardware buttons 204.

A Windows Internet (WinINet) API 220 represents a set of functions that enable applications to access a packet network such as the Internet. For example, the WinINet API 220 could interact with the Gopher protocol, the file transfer protocol (FTP), and the hypertext transfer protocol (HTTP) to access the packet network. A Pocket Internet Explorer (IE) 222 allows a user to view web pages. As a particular example, the web pages may be displayed on a virtual 640×480 display. Various protocols 224, such as hypertext markup language (HTML), JavaScript, extensible markup language (XML), or extensible style language (XSL), can be used to transport data over the packet network.

Tools 226 support the programming of various applications. For example, the tools 226 could represent the Microsoft Embedded Visual Tools (MSEVT) toolkit that supports programming using Visual Basic and Visual C++. Other programming languages could be used to generate an application that is operating on the handheld device 200. In another embodiment, the tools 226 may be used to generate an application, and the tools 226 need not reside on the handheld device 200.

An application 228 represents an application that can be executed by the medical device 200. For example, the application 228 could represent a medical program, such as a program to control the operation of the implanted components 108a, 108b. Any suitable number of applications 228 maybe used in the medical device 200.

Figure 2B:
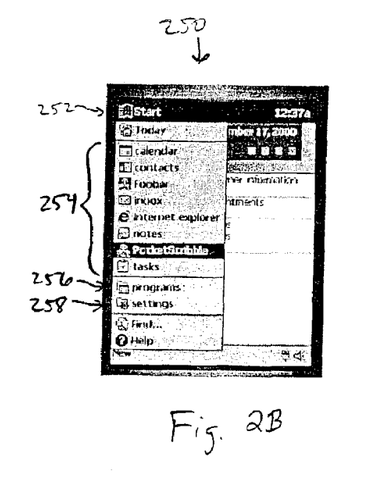

As shown in FIG. 2B, when the medical device 200 is activated, a display 250 is presented to the user. The display 250 represents a user interface, which includes a Start menu 252. When the user uses a stylus or other input device to press a button and reveal the Start menu 252, various items that can be selected are displayed to the user. Among other things, the Start menu 252 may identify one or more applications 254 that can be selected by the user and executed by the device 200. The Start menu 252 may also include a Programs item 256, which also identifies various applications that can be executed by the device 200. In a particular embodiment, the Programs item 256 includes sub-folders, such as a "games" sub-folder that identifies various gaming applications that can be executed. In addition, the Start menu 252 may include a Settings item 258.

Figure 2C:
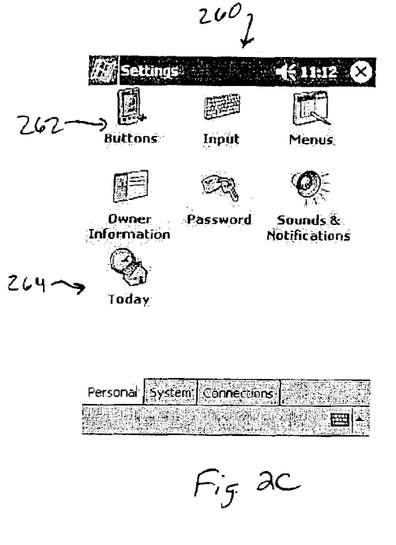
Figure 2D:
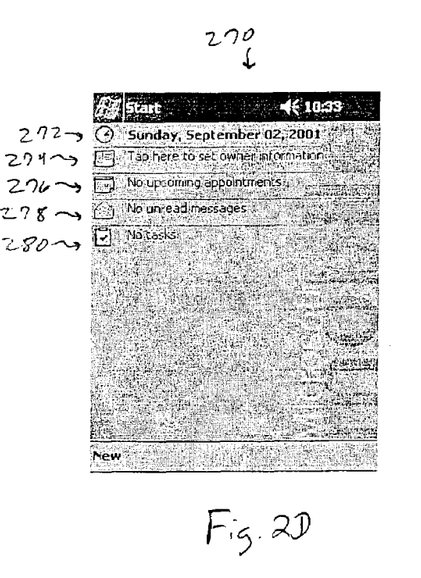

As shown in FIG. 2C, when the user selects the Settings items 258, a Settings menu 260 is displayed. The Settings menu 260 allows the user to control different aspects of the handheld device 200. For example, the Settings menu 260 may include a Buttons group 262, which allows the user to assign and control the functions associated with the buttons 204. The Settings menu 260 may also include a Today group 264. Selecting the Today group 264 causes the handheld device 200 to display the Today screen 270, which is shown in FIG. 2D. In FIG. 2D, the Today screen 270 includes a date 272, owner information 274, a calendar 276, an inbox 278, and tasks 280. These represent various system functions provided by the operating system executed by the medical device 200.

The medical device 200 illustrated in FIG. 2A and the screenshots 250, 260, 270 illustrated in FIGS. 2B through 2D are for illustration only. Other medical devices or screenshots could be used. For example, the medical device 200 could use any other suitable application stack 210.

Figure 3:
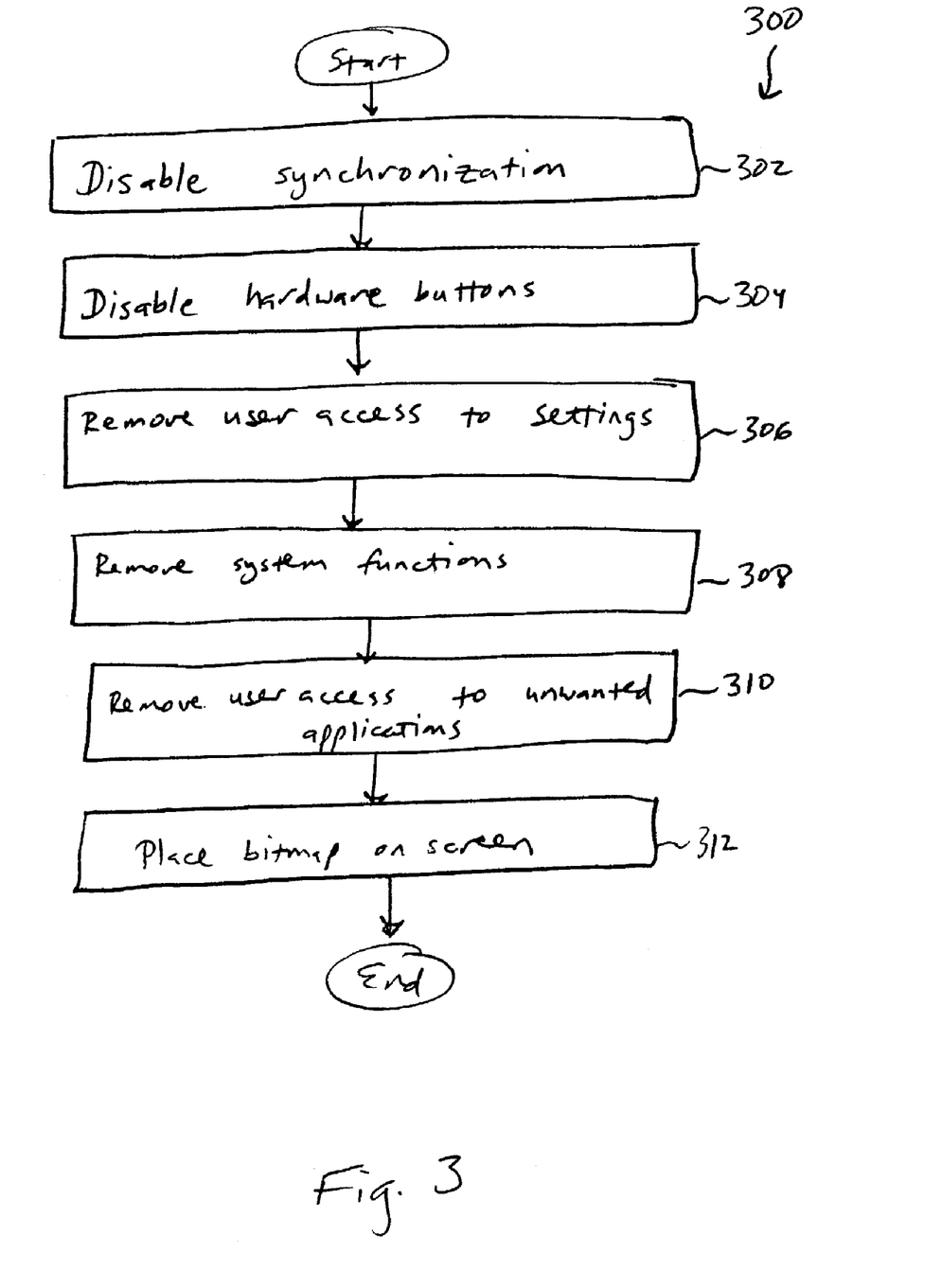
FIG. 3 illustrates an example method for securing the operating system in a handheld medical device according to one embodiment of this disclosure.

FIG. 3 illustrates an example method 300 for securing (or locking down) the operating system in the medical device 200 according to one embodiment of this disclosure. The method 300 may be described with respect to the medical device 200 of FIG. 2 operating in the medical system 100 (as the handheld programmer 104) of FIG. 1.

The synchronization mechanism of the handheld device 200 is disabled at step 302. Disabling this mechanism will disable the ability of the medical device 200 to synchronize with the base computer 102 through the docking cradle 114.

At least some of the buttons 204 of the medical device 200 are disabled at step 304. This may include, for example, assigning no function to the buttons 204 typically associated with the calendar, mail, task, contact, and record functions. This may also include allowing the power button 204 to retain its normal function.

User access to one or more settings is removed at step 306. This may include, for example, removing or deleting the Buttons group 262 from the Settings menu 260. This may reduce or eliminate the likelihood that a user of the medical device 200 will be able to reassign functions to the disabled buttons 204. At this point, the disabled buttons 204 cannot be used to invoke execution of applications that may interfere with the medical programs on the handheld device 200. Removing the user access to the settings may also include removing or deleting the Today group 264 from the Settings menu 260. The removal or deletion of the Buttons group 262 and the Today group 264 from the Settings menu 260 removes user access to these settings on the handheld device 200. Other settings could also be disabled or removed.

One or more system functions are removed at step 308. This may include, for example, removing or deleting the date 272, owner information 274, calendar 276, inbox 278, and tasks 280 from the Today screen 270. These features could possibly interfere with the medical programs executed by the medical device 200. By removing these features from the Today screen 270, these features may be disabled.

User access to one or more unwanted applications is removed at step 310. The unwanted applications could represent applications 254 contained in the Start menu 252 or applications listed by the Programs item 256. As a particular example, the applications could include Microsoft Internet Explorer. These applications could possibly interfere with the medical programs executed by the medical device 200. Without user access, a user may be prevented from executing these applications.

Optionally, a bitmap may be placed on the display 202 of the medical device 200 at step 312. This may include, for example, placing a logo or any other suitable bitmap on the display 202.

These steps are generally performed by execution of a program install or autorun of the selected application (securing or lock down program) executed by the processor 206 of the medical device 200. For example, the program may be stored in the memory 208, and in one embodiment, is stored in a non-volatile portion of the memory 208. In this way, the program will remain intact in the memory 208 in the event the medical device 200 loses power. Also, the program may be executed automatically, such as by configuring an "autorun.exe" program in the medical device 200 to execute the procedure, or manually. If automatic, the procedure is executed automatically when power is restored to the medical device 200 after a power failure. By storing the procedure in the non-volatile portion of the memory 208 and automatically executing the procedure, the medical device 200 may be configured properly even after a system reset occurs.

The program performs the steps or acts identified in the method 300 of FIG. 3. Though not all steps may be necessary, the program secures, or locks down, the operating system of the medical device 200 to prevent or reduce potential interference with the medical application program 228 executing on the medical device 200. Such securing or locking down of the operating system further includes preventing an unauthorized user from downloading additional programs, modifying any existing programs, or in other ways interfering with the operation of the medical application program 228 (either intentionally or unintentionally), and reducing or eliminating any other interference that may exist from, or be caused by, directly or indirectly, normal operation of the operating system.

In another embodiment, the procedure may be stored on a security card, such as a Security Digital card. In this embodiment, the program may be executed by insert the Security Digital card into the handheld device 200.

In another aspect of this disclosure, there is provided a method of converting a general computing device having an operating system into a medical device 200. The medical program 228 is loaded into the medical device 200. A securing program is loaded into the medical device 200 and executed. The operating system of the medical device 200 is secured, or locked down, in response to execution of the securing program. This securing or locking down acts to prevent an unauthorized software modification to the computing device, and thereby converting the computing device into a medical device. In this document, the phrase "software modification" refers to any addition, modification, or deletion of software on the device 200, including but not limited to adding new software and modifying existing software.

In yet another embodiment, there is provided a method of converting a computing device including at least one medical program 228 into the medical device 200. While operating under a Windows-based operating system, the computing device is loaded with a securing program that disables the Windows-based operating system sufficiently to prevent unwanted potential interference with the execution of the medical program 228. Further, one or more buttons (such as the record and contacts buttons) or features (such as the synchronize and today features) can be left enabled as required per the particular application of the device. In this document, the term "interference" refers to any adverse or undesired interaction between two or more applications, including but not limited to one application preventing the execution of another application or preventing the proper operation of another application.

Although FIG. 3 illustrates one example of a method 300 for securing the operating system in a handheld medical device, various changes may be made to FIG. 3. For example, no bitmap need be placed on the display 202 of the handheld device 200 at step 312. Also, the various steps in FIG. 3 could be performed in any suitable order.

It may be advantageous to set forth definitions of certain words and phrases that may be used within this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A method of converting a personal digital assistant (PDA) into a controller device for an implantable medical device, the PDA comprising an operating system, the method comprising:

installing a medical program on the PDA, the medical program allowing a user of the PDA to control operations of the implantable medical device; and installing a securing program on the PDA such that the securing program is executed on the PDA whenever the PDA is reset;

wherein upon execution, the securing program is operable to modify the operating system of the PDA to secure the operating system to prevent interference with operations of the medical program by:

(i) disabling a synchronization mechanism of the PDA that automatically synchronizes data with one or several other computing devices;

(ii) changing operating system settings associated with hardware buttons of the PDA to prevent execution of previous operating system enabled functions associated with the hardware buttons;

(iii) modifying an operating system menu to remove user access to selected operating system settings that permit user modification of assignment of functions to the hardware buttons; and (iv) disabling selected operating system enabled functions.

2. The method of claim 1 wherein the securing program is further operable to disable access to one or more applications packaged with the operating system.

3. The method of claim 1 wherein one of the applications to which access is disabled is an internet browser application.

4. A personal digital assistant (PDA) device adapted to control an implantable medical device, comprising:

an operating system;

a medical device program for providing a user interface to control operations of the implantable medical device; and a securing program that is automatically executed whenever the PDA is reset;

wherein upon execution, the securing program is operable to modify the operating system of the PDA to secure the operating system to prevent interference with operations of the medical program by:

(i) disabling a synchronization mechanism of the PDA that automatically synchronizes data with one or several other computing devices;

(ii) changing operating system settings associated with hardware buttons of the PDA to prevent execution of previous operating system enabled functions associated with the hardware buttons;

(iii) modifying an operating system menu to remove user access to selected operating system settings that permit user modification of assignment of functions to the hardware buttons; and (iv) disabling selected operating system enabled functions.

5. The PDA of claim 4 wherein the securing program is further operable to disable access to one or more applications packaged with the operating system.

6. The PDA of claim 4 wherein one of the applications to which access is disabled is an internet browser application.

7. The PDA of claim 4, wherein:

the one or more operating system settings comprise operating system settings for a buttons group and a today group in a settings menu on the PDA; and the one or more system functions comprise a date function, a calendar function, an inbox function, an owner information function, and a task function from a today screen on the PDA.

\* \* \* \* \*